United States Patent [19]

Curry et al.

[11] Patent Number: 4,719,290
[45] Date of Patent: Jan. 12, 1988

[54] COMPOSITION OF INTRAVENOUS IMMUNE GLOBULIN

[75] Inventors: Willie M. Curry, New Rochelle; David L. Farb, LaGrangeville, both of N.Y.

[73] Assignee: Armour Pharmaceutical Corporation, Fort Washington, Pa.

[21] Appl. No.: 614,005

[22] Filed: May 25, 1984

Related U.S. Application Data

[60] Division of Ser. No. 529,079, Sep. 2, 1983, Pat. No. 4,482,483, which is a continuation-in-part of Ser. No. 482,699, Apr. 6, 1983, abandoned.

[51] Int. Cl.$^4$ .................... C07G 7/00; A61K 35/10; A61K 39/00
[52] U.S. Cl. .................... 530/387; 530/363; 424/85; 424/87; 424/101; 514/2; 514/6
[58] Field of Search ............... 530/350, 351, 387, 363; 424/85, 87, 101; 514/2, 6

[56] References Cited

U.S. PATENT DOCUMENTS

| | | | |
|---|---|---|---|
| 2,520,076 | 8/1950 | Williams et al. | 530/387 |
| 3,903,262 | 9/1975 | Pappenhagen | 530/387 |
| 4,021,540 | 5/1977 | Pollack et al. | 424/86 |
| 4,124,576 | 11/1978 | Coval | 530/387 |
| 4,126,605 | 11/1978 | Schneider et al. | 530/389 X |
| 4,168,303 | 9/1979 | Nishida et al. | 530/387 |
| 4,379,086 | 4/1983 | Kimura et al. | 424/101 X |
| 4,396,608 | 8/1983 | Tenold | 424/101 X |
| 4,515,776 | 5/1985 | Taniguchi et al. | 530/387 |

OTHER PUBLICATIONS

Smyth, Jr. et al., *Industrial Hygiene and Toxicology* 2nd Ed. "The Toxicology of the Polyethylene Glycols", pp. 7–12, 1950.

Miler et al., *J. Med. Microbiol.*, vol. 10, pp. 19–27, 1977.

*Primary Examiner*—Lionel M. Shapiro
*Assistant Examiner*—Robin Lyn Teskin

[57] ABSTRACT

An intravenous immune globulin preparation having at least 99% pure globulin protein and an anticomplement activity of less than 0.10 C'50 units/mg IgG prepared by: precipitating impurities from Cohn Fraction II in an aqueous-alcohol medium at defined temperature and pH, removing the precipitated impurities, stabilizing the diluted solution with albumin, concentrating the solution and removing the alcohol therefrom. Also prepared by this method, an intravenous, hyperimmune globulin preparation having increased antibody titers to sixteen serospecific strains of Pseudomonas aeruginosa.

12 Claims, No Drawings

COMPOSITION OF INTRAVENOUS IMMUNE GLOBULIN

RELATED APPLICATIONS

This application is a divisional of our copending application Ser. No. 529,079 filed Sept. 2, 1983, now U.S. Pat. No. 4,482,483, which in turn is a continuation-in-part of application Ser. No. 482,699 filed Apr. 6, 1983, now abandoned.

BACKGROUND OF THE INVENTION

1. Field of the Invention

The present invention relates to high purity intravenously injectable gamma globulin (IgG) preparations and a process for preparing the same. More particularly, the invention relates to a product and method of making unmodified, unaltered, undenatured or native gamma globulin molecules of high purity for intravenous administration.

The invention also relates to high purity intravenous hyperimmune globulin preparations having increased antibody titers to sixteen serospecific strains of *Pseudomonas aeruginosa* and the method of making such preparations.

It has been known for some time that certain patients with humoral immunodeficiencies are susceptible to acute and chronic infections which sometimes assume life-endangering dimensions. These patients are not able to produce the required levels of antibodies and the same must be supplied to them for the prevention and treatment of such infections.

The immune globulin fraction of pooled human plasma contains antibodies to many viruses and bacteria and thus is effective in the management of various diseases including those associated with Staphylococci, Streptococci, Coli, Pseudomonas, *Herpes zoster* and *pyocyaneus septicemias.*

Patients with normal levels of antibodies also require additional defense in overcoming serious infections such as caused by *Pseudomonas aeruginosa.*

Immunogenic pseudomonas vaccines and globulins having raised titers of protective antibody and increased phagocytic activity were found effective in the treatment of infections caused by *Ps. aeruginosa.*

Human immune globulins were first isolated on a large scale during the 1940's by F. J. Cohn. It was also observed that the aggregate formed during the fractionation procedure results in anticomplement activity and that clinical application causes adverse reactivity in the patient.

2. Description of the Prior Art

It has been known to prepare immune globulin containing antibodies by fractioning human blood plasma according to the so-called Cohn-method. It has also been known to further purify immune globulin for administration either intramuscularly or intravenously. While producing some of the desired effects, both kinds of administration have some disadvantages, which at times, may be serious or even life-threatening.

Intramuscular injections of immune globulin have proven effective in raising the level of circulating immune globulin and in decreasing the length, frequency and severity of infections in some patients. There are patients, however, who cannot achieve adequate immune globulin levels and protection from infection with intramuscular administration of immune globulin. Such patients when treated via plasma therapy experience improvement which indicates that intravenous administration may have advantages over the intramuscular route. Other disadvantages of intramuscular administration of immune globulin include the delayed onset of reaction resulting from the slow diffusion of the substance into the circulation, and inconsistent absorption and local degradation in the muscle where the injection is administered.

With intravenously administered immune globulin adequate levels of circulating antibody could be reached immediately and controlled by the rate of infusion. The intravenous route of administration also overcomes the effects of inconsistent absorption and local degradation in the muscle. Also, patients with small muscle mass or bleeding tendency tolerate an intravenous injection better than an intramuscular injection.

While intravenous administration is the preferred route of administration, the product so administered is not without some serious drawbacks. It is known that intravenously administered immune globulin may cause unpleasant side effects such as flushing, wheezing back and muscle pain, anxiety and hypotension. It has been observed that these side effects may be due to the activation of complement, secondary to the formation of immune complexes, aggregates of immune globulin and denatured globulin formed during the storage thereof.

The prior art has made great efforts to prepare immune globulin which has lesser anticomplement activity, mainly by decomposing or removing the aggregated or denatured globulin. Such efforts included: enzymatical hydrolysis using pepsin, plasmin, papain, or bacterial proteases; chemical tratment by an acid, propiolactone or the like; conversion of the immunoglobulin into a chemical derivative such as by amidation, alkylation or S-sulfonation; and fractional precipitation of the immunoglobulin using polyethylene glycol or the like.

While these methods seemed to decrease the presence of aggregated or denatured globulin in the final products and consequently lowered the anticomplement activity, they were not without other shortcomings, such as low activity of the antibody, shortened half-life time of the immunoglobulin in the blood, and the presence of some denatured impurities which is believed to cause a decrease in efficacy of the immunoglobulin.

To overcome the above-mentioned disadvantages, the prior art has further proposed various preparative methods for intravenous immunoglobulin. Illustrative of these are the methods disclosed in the following patents:

U.S. Pat. No. 4,256,631 discloses a process for the preparation of immunoglobulin for intravenous administration comprising the purification of immunoglobulin by a combination of a fractional precipitation method in which one or more divalent or trivalent metal salts are added to an aqueous solution of the immunoglobulin and the supernatant is processed by affinity chromatography using as an adsorbant a complex of human IgG and a polyhydroxy polymeric compound. The resultant immunoglobulin is said to be extremely pure.

U.S. Pat No. 4,305,870 pertains to a method for making intravenous plasma derivatives which includes the steps of mixing bentonite and an aqueous solution of plasma derivatives containing exogenous activity, the bentonite and the mixing time being sufficient to adsorb exogenous activity, and isolating the aqueous phase from the bentonite. Optionally, for the removal of residual exogenous activity, the bentonite-treated aqueous phase is further purified by ion-exchange chromatography. The so-obtained product is said to have an acceptable low content of externally deleterious or exogenous activity.

While the above-noted attempts by the prior art greatly enhanced the success of treatment of various infectious diseases by producing satisfactory immunoglobulin for such treatment, none to our knowledge has produced a natural, unmodified, unaltered and undenatured product which desirably should have the following characteristics: it should contain substantially pure Immunoglobulin G (IgG) so that it is substantially free of naturally occurring IgA and IgM antibodies; it should contain all subclasses of IgG, namely $IgG_1$, $IgG_2$, $IgG_3$, and $IgG_4$ in substantially the ratio as they occur in blood plasma; spontaneous complement activation should be very low or absent; it should be free of polymeric IgG; and it should have a very low level of trace constituents, such as enzymes which tend to degrade and destabilize IgG during storage.

The underlying reason for the production of such a natural product will be easily ascertained by those skilled in the art from the following brief explanation.

The native IgG molecule is known to have two types of biological activities, namely, the immune-specific activity and the non-immune-specific or "effector" activity. The immune-specific activity is characterized by binding properties for specific antigens whereby the IgG molecule acts as an antibody. The non-immune-specific or "effector" activity includes binding and activation of complement, opsonic activity, and the binding to specific cellular receptors for the Fc portion of the molecule. Any change in the native IgG molecule which alters, reduces or eliminates either of these two types of activities is referred to as denaturation whether said denaturation is the result of intentional or unintentional chemical or enzymatic modification. Commercial preparations of intramuscular IgG, which are processed withouth chemical modifications, contain aggregated forms of IgG that cause high levels of spontaneously fixed and activated complement and are examples of unintentional denaturation. Examples of intentionally denatured IgG molecules include IgG preparations that are modified with the use of chemicals and/or enzymes in an attempt to improve the safety of intravenous administration. Such intentional denaturation diminishes or even completely eliminates the effector functions of IgG and reduces the total beneficial biological potency of the IgG.

In addition to the desired characteristics described above, a Pseudomonas immune globulin preparation must possess preformed, specific anti-Pseudomonas antibodies. Host defense for Pseudomonas depends upon the presence of adequate numbers of functional phagocyte cells plus serum opsonic activity. Optimal phagocytosis of Pseudomonas occurs in the presence of type-specific Pseudomonas antibody. At least seventeen separate strains of *Ps. aeruginosa* have been identified by the World Health Organization, many of which show unusual resistance to treatment with antimicrobial drugs. Each strain is characterized by localized infections that may overwhelm the host tissue. Endotoxin, toxin A, elastase and protease are released to further weaken the host's defensive mechanism. Clinical cases in which normal immune defenses are compromised, such as burn, cancer and cystic fibrosis cases are particularly susceptible to infection by *Ps. aeruginosa*. A fast acting intravenous injection of hyperimmune, polyvalent gamma globulin to enhance specific antibody activity can be of life-saving to these patients.

Anti-Pseudomonas immune globulin, immune whole blood and immune plasma are known in the prior art. Notwithstanding their beneficial properties, their drawbacks include having limited antibody titers, protection against only some of the recognized strains of *Ps. aeruginosa*, and the lack of high purity.

It is, accordingly, an object of the present invention to provide a native gamma globulin preparation suitable for intravenous injection.

It is another object of the present invention to eliminate undesired denatured properties of IgG not by the alteration of effector functions but by the selective elimination of molecular forms of IgG which are denatured and at the same time eliminate impurities in the form of non-IgG proteins.

It is still another object of the present invention to provide a gamma globulin preparation suitable for intravenous administration, in which anticomplement activity is less than about 0.1 $C'50$ units/mg.

It is a further object of the present invention to provide a gamma globulin preparation containing at least 99.0% pure immune gamma globulin which is essentially free of IgA and IgM.

It is also an object of the present invention to provide a gamma globulin preparation containing all subclasses of IgG, namely $IgG_1$, $IgG_2$, $IgG_3$, and $IgG_4$, in substantially the ratio as occurring in normal blood plasma.

A further object of the present invention is to provide an intravenous, hyperimmune globulin preparation with increased antibody titers to sixteen serospecific strains of *Pseudomonas aeruginosa*.

A still further object of the present invention is to provide an intravenous, hyperimmune globulin preparation with increased antibody titers to sixteen serospecific strains of *Pseudomonas aeruginosa* in which anticompliment activity is less than about 0.1 $C'50$ units/mg.

Another object of the present invention is to provide an intravenous, hyperimmune globulin preparation which is essentially free of IgA and IgM.

It is still another object of the present invention to provide a simple economical process for commercial preparation of immune gamma globulin.

These and other objects and advantages of the present invention will be readily apparent to those skilled in the art from the description of the invention that follows.

SUMMARY OF THE INVENTION

According to the present invention, an unaltered, unmodified, undenatured or native immune gamma globulin preparation is provided for intravenous administration. Said preparation comprises at least 99.0% human native gamma globulin which has undergone no chemical or enzymatic modification, contains less than 0.1% IgA, essentially no IgM or aggregates and has an anticomplement activity of 0.1 or less $C'50$ units/mg. The immune gamma globulin preparation of the present invention consists of all the subtypes of IgG in approximately the same ratio as present in the starting material namely, about 64% $IgG_1$, 29% $IgG_2$, 6% $IgG_3$ and 1% $IgG_4$.

The anti-Pseudomonas hyperimmune globulin embodiment of the present invention, in addition to having the above-described characteristics of immune gamma globulin, also possesses increased anti-body titers against sixteen serospecific strains of *Pseudomonas aeruginosa*. Hyperimmune globulin products herein referred to denote products having a greater quantity of antibodies than the quantity found in blood products obtained from un-immunized donors.

The process for the preparation of IgG includes the steps of:
a., precipitation impurities from Cohn Fraction II or plasma fraction harvested by plasmaphoresis in an aqueous-alcohol medium at a temperature of about 1°-10° C. and at a pH of about 7 to 9;
b., removing the precipitated impurities;
c., stabilizing the solution with albumin; and
d., concentrating the solution and removing the alcohol therefrom.

The concentrated solution is formulated by the addition of a salt and/or with carbohydrates. The formulated IgG is sterile filtered and dispensed in vials.

DETAILED DESCRIPTION OF THE INVENTION

According to the present invention, the process for preparing the immune gamma globulin comprises the steps of:
a., suspending proteins present in Cohn Fraction II obtained from normal or hyperimmune plasma in an aqueous solution of about 0 to 16% w/v and preferably about 2 to 10% w/v alcohol at a protein concentration of about 1 to 8% w/v and preferably about 1 to 4% w/v at a temperature of 1°-19° C. and preferably 2°-5° C.;
b., adjusting the pH of the suspension to about 7.8±0.4 and preferably to about 7.6±0.2;
c. adding NaCl to the suspension to obtain a salt concentration of 0 to 2 mM NaCl.
d., allowing the suspension to stand for 2 to 24 hours and preferably 6 to 18 hours to precipitate IgM, IgA, enzymes and polymeric forms of IgG impurities and to obtain equilbrium between precipitated impurities and dissolved IgG;
e., removing the precipitated impurities by filtration or centrifugation to obtain a dilute IgG solution;
f., stabilizing the dilute IgG solution by adding purified Human Serum Albumin to obtain an IgG/albumin ratio of 1/1 to 5/1 and preferably of 1/1 to 2/1;
g., adjusting NaCl concentration of the solution to 0 to 0.9% w/v NaCl;
h., adjusting the pH of the solution to about 6.9±0.4;
i., concentrating the solution by ultrafiltration to obtain a concentration of 3.8 to 4.5% w.v IgG and preferably to about 4% w/v IgG;
j., removing the alcohol and concentrating the solution to about 4 to 6% w/v IgG by diafiltration; and
k., formulating the solution with the addition of sodium chloride and/or with a carbohydrate.

According to the present invention, it has been found that impurities from native IgG can be separated without the use of chemicals that tend to denature IgG under precisely established conditions which are not suggested by the prior art and not predictable from the known behavior of the compounds used in the process. The conditions essentially consist of using low ionic strength alcohol solution, and cryoprecipitation at specific temperatures and pH.

Starting Materials for the Preparation of Anti-Pseudomonas Hyperimmune Globulin The polyvalent anti-Pseudomonas hyperimmune globulin of the present invention is produced by first isolating and combining immunizing antigens obtained from particular strains of *Pseudomonas aeruginosa* for use in a polyvalent vaccine which is capable of immunizing against any of sixteen recognized serotypes of *Pseudomonas aeruginosa* infection. Human volunteers then are vaccinated with the polyvalent vaccine to elicit responses in the antibody titers to all sixteen serotypes, followed by obtaining plasma from vaccinated donors and purification of the resultant high titer gamma globulin.

The prior art has used alternative serotyping schemes for *Ps. aeruginosa*, however, these are now being superseded by an internationally-approved serotyping system based, in the main, on Habs original work (Habs, I. Zs chr. f. Hyg. 144: 218–228, 1957). The sixteen strains used in the present invention have been serotyped by the Central Public Health Laboratory, Colindale, London and are stored in lyophilized form under security in the Wellcome Bacterial Culture Collection, London. Table I shows the sixteen serotypes under Wellcome Bacterial Collection and Designation Number and correspondence with the Habs serotypes.

TABLE I

| Strains of *Ps. aeruginosa* Used for Production of Pseudomonas Vaccine | | |
|---|---|---|
| Serotype | Wellcome Bacterial Collection No: (CN) | Wellcome Designation No. |
| HABS 1 | 6669 | 1 |
| HABS 2 | 6670 | 2 |
| HABS 3 | 6766 | 3 |
| HABS 4 | 6767 | 4 |
| HABS 5 | 6674 | 5 |
| HABS 6 | 6675 | 6 |
| HABS 7 | 6768 | 7 |
| HABS 8 | 6677 | 8 |
| HABS 9 | 6777 | 9 |
| HABS 10 | 6789 | 10 |
| HABS 11 | 6782 | 11 |
| HABS 12 | 6709 | 12 |
| VERNON 13 | 6710 | 13 |
| MEITERT 10 | 6821 | 14 |
| HOMMA 11 | 6787 | 15 |
| HOMMA 13 | 6788 | 16 |

The procedure of isolating the antigens, preparing the polyvalent vaccine, immunizing volunteers and obtaining plasma therefrom is based on known techniques utilized by the prior art.

Vaccine

The vaccine may be prepared according to a publication by Miler et al, J. Med. Microbiol. Vo. 10, pp. 19–27, 1977.

Sixteen of the recognized virulent serotypes of *Pseudomonas aeruginosa* were identified in separate clinical isolates and cultured as sixteen separate master serotype broths. Each master culture was grown in the presence of ammonium lactate and other nutrients. (Aliquots of each master culture were frozen as starting materials for subsequent vaccine preparation.) The microorganisms were harvested by centrifugation, washed by resuspension and centrifugation in fresh media, then resuspended in an extraction solution containing glycine and ethylenediamine tetraacetic acid. The microorganisms were removed by centrifugation and destroyed. The extraction solution contains cell wall components from the bacteria that are serotypically characteristic of each strain. The fresh extracts were treated with formalin to minimize toxicity. The ethylenediamine tetraacetic acid and excess formalin were removed by dialysis and the extracts are concentrated until one ml of solution represents extract from $10^8$ bacteria. Mice were immunized with each of the sixteen monovalent vaccines to elicit antibody responses corresponding to the bacterial strain, showing serospecificity in each case. The results were determined by the Enzyme-Linked Immunosorbent Assay (ELISA).

ELISA assay

The Elisa assay employing goat anti-human immunoglobulin G(IgG) conjugated with alkaline phosphatase (Sigma Chemical Co.) and p-nitrophenyl phosphate (Sigma Chemical Co.) as a indicator system is used for measurement of antibody response to the 16 individual pseudomonas serotypes contained in The Wellcome Pseudomonas Vaccine.

In brief, wells of Immunlon I polystyrene microtiter plates (Dynatech Labs) are coated with 50 µl of the individual serotype antigens in 0.1M glycine buffer (pH 9.5) by incubating at 4° C. for four hours. Optimal concentration of each serotype antigen is determined by block titration against Wellcome polyvalent pseudomonas antibody control. At the end of the incubation period, the plates are washed four times with 0.02M PBS-Tween 20 (pH 7.2).

Sera samples starting with a 1:50 dilution in PBS-Tween is diluted in twofold steps in 50 µl amounts using an autodilutor (Dynatech Labs). The plates are then incubated at room temperature for three hours. Each plate contains appropriate positive and negative controls. After incubation, the plates are washed three times with PBS-Tween.

A predetermined optimal dilution of anti-human IgG conjugated with alkaline phosphatase in PBS-Tween is made and 50 µl is dispensed into each wall of the microtiter plates. The plates are then incubated at room temperature for one hour. After incubation, the plates are washed four times in PBS-Tween and 50 µl of 1 mg/ml p-nitrophenyl phosphate in 10% diethanolamine (pH 9.8) is added. The plates are then incubated at 4° C. for 18 hours.

After incubation, 50 µl of quenching solution 0.1M EDTA (pH 7.0) is added to each well. Optical density is determined spectrophotometrically for each well solution using a recording automatic spectrophotometer (Dynatech).

The antibody titer is determined by the maximal dilution of sample that gives an optical density of 0.3 or greater.

Generally, a correlation was found between a monovalent vaccine and consequent response thereto by innoculated mice, i.e. each serotype monovalent vaccine elicits an immune response to the particular serotype. A study by R. J. Jones and E. A. Roe (Br. J. Exp. Path. 56: 34–43, 1975) shows similar findings using haemagglutination assay.

Immunization

For human vaccination each of the sixteen nonovalent vaccines was blended and concentrated such that 1 ml of solution represents extract from $10^8$ bacteria of each strain. One ml of the polyvalent vaccine was injected s.c. in volunteers three times at one week intervals to elicit antibody production.

An increase in plasma titer of antibodies for each of the sixteen serotypes occurred. Table II shows, however, that some individuals respond with a high average titer while others response with much lower titers as determined by the ELISA assay. The response as expressed by titer is usually maintained at a high level between three to six weeks post vaccination.

TABLE II

| | Average of 16 Serotype Responses Relative to each Individual Zero Day Titer | |
|---|---|---|
| Days Following Immunization | High Response Group (15 Volunteers) | Low Response Group (13 Volunteers) |
| 0 | 1.0 | 1.0 |
| 21 | 12.1 | 3.7 |
| 42 | 6.5 | 2.2 |
| 70 | 3.4 | 1.6 |
| 98 | 2.9 | 1.4 |
| 126 | 2.1 | 1.3 |

Accordingly, the time of collection of blood from immunized donors is of an important factor in obtaining immune globulin products having a high antibody level. Generally, about 3 weeks post immunization the antibody level appears to be the highest and decreases gradually thereafter.

Plasma Selection

The antibodies generated by human volunteers as a result of vaccination are harvested by plasmapheresis. Table III shows titer values on plasma pools obtained from 28 immunized donors, one group of which had high response and the other low response to immunization. It is also noted that plasma isolated from non-immunized donors also contains low titers of antibody to each of the sixteen serotypes of Ps. aeruginosa.

TABLE III

RELATIVE RESPONSES IN THE TITER FOR EACH SEROTYPE OF PSEUDOMONAS AERUGINOSA IN SELECTED PLASMA POOLS

| | High Response Group | | Low Response Group | |
|---|---|---|---|---|
| Serotype | Pre-Vaccination | 21 Day Plasma Pool | Pre-Vaccination | 21 Day Plasma Group |
| 1 | 200 | 800 | 200 | 800 |
| 2 | 400 | 800 | 200 | 800 |
| 3 | 400 | 800 | 200 | 400 |
| 4 | 200 | 800 | 100 | 400 |
| 5 | 400 | 1600 | 200 | 800 |
| 6 | 100 | 800 | 50 | 200 |
| 7 | 200 | 800 | 50 | 400 |
| 8 | 200 | 800 | 100 | 400 |
| 9 | 200 | 800 | 200 | 400 |
| 10 | 200 | 1600 | 50 | 400 |
| 11 | 400 | 800 | 200 | 800 |
| 12 | 200 | 1600 | 200 | 400 |
| 13 | 25 | 800 | 25 | 400 |
| 14 | 400 | 1600 | 400 | 400 |
| 15 | 100 | 800 | 100 | 400 |
| 16 | 400 | 1600 | 200 | 400 |

Purification of Polyvalent Gamma Globulin

While both plasma pools, one having low and the other high antibody titer levels, may be used to produce immune gamma globulin, high titer plasma is preferred for use as starting material for the preparation of hyperimmune gamma globulin.

Before purification by the process of the present invention, coagulation factors, Factor VIII and Factor IX Complex are removed and the plasma subjected to Cohn fractionation. The purification procedure starts with the plasma fraction which is substantially equivalent to the Cohn Fraction II material.

Starting Materials for the Preparation of Immune Globulin (Normal Immune Globulin)

The starting material for normal immune gamma globulin may be the well-known Cohn Fraction II paste, or other starting materials having native IgG and its subclasses present. However, it is preferred to use Cohn Fraction II which has a history of safety and efficacy as a therapeutic product in the intramuscular dosage form and is commercially available. Alternatively, the active ingredient may be obtained by processing human plasma from which the coagulation factors, Factor VIII, and Factor IX Complex, are removed before the plasma is subjected to Cohn Fractionation. Following the removal of Factor VIII and Factor IX, the Cohn cold-ethanol fractionation produces a series of protein fractions: Fraction I, Fraction II+III, Fraction $IV_1+IV_4$ and Fraction V. In addition to IgG, IgM and IgA, Fraction II+III is enriched in lipids, lipoproteins, pigmented materials such as carotinoids, as well as proteolytic enzymes. All of these substances must be separated from the IgG. After the separation of these undesirable substances, Fraction II is about 95% pure IgG and it represents about 40 to 50% of the IgG content of the starting plasma. Fraction II is comprised of all four subclasses of IgG, namely, $IgG_1$, $IgG_2$, $IgG_3$ and $IgG_4$, in a similar ratio as that found in plasma. The 95% pure IgG is not suitable for direct formulation into an intravenous product for several reasons. IgG is easily denatured and as such, can form large high molecular weight aggregates. These aggregates can fix complement in the absence of antigen triggering a complement cascade which can be a risk to patients receiving intravenous infusions of IgG. The impurities amounting to about 5% in Cohn Fraction II are also undesirable, such as: IgM, which is easily denatured and readily fixes complement; IgA, which is known to cause anaphylactoid reactions in IgA-deficient patients; Pre-Kallikrein Activator which causes vasoactive effects on administration; Plasminogen/Plasmin, which can fragment IgG and lead to reduced circulatory half-life. Cohn Fraction II, therefore, is further purified and the native character of the molecule is preserved by careful handling and stabilization as further described in detail in the method of the present invention.

Process of Preparing IgG

Cohn Fraction II paste or its equivalent is suspended and soluble portions thereof is dissolved in an aqueous alcohol solution. While the preferred alcohol is ethanol, other pharmaceutically acceptable alcohols may also be used. Subsequent to precipitating the impurities consisting of IgM, IgA, enzymes, polymeric forms of IgG and other trace contaminants, the same are removed by either filtration or centrifugation. The filtration may be accomplished by adding a diatomaceus earth filter aid, such as Hyflo-Super Cel, to the suspension, mixing the same with the suspension and filtering through 0.2 to 0.5 micron filter pads, such as Cuno 60SP. Alternatively, the precipitate may be removed by centrifugation using conventional equipment. The filtrate is concentrated by ultrafiltration over semipermeable membranes such as Pellicon system containing PT series membranes with a 10,000 or 20,000 m. w. limit in conjunction with a 1.5 micron filter, such as a Pall filter cartridge. The pH is adjusted to 7.3±0.5, albumin is added to stabilize the purified gamma gloubulin and NaCl is added to improve the solubility. The alcohol is removed from the IgG solution by diafiltration at constant volume using 5 to 10 volumes of 0.2% w/v NaCl. After the removal of the alcohol the solution is concentrated further to about 6.0% w/v IgG. The alcohol-free IgG/albumin solution is adjusted to pH 6.9±0.4 using citric acid. This solution then is diluted to contain about 5% w/v IgG by formulating the same with a salt or sugar solution. If formulated with salt, the final concentration of salt should be about 0.9% w/v. If formulated with sugar, the sugar concentration, in general, should be in the range of about 2.5 to 10% w/v. Such concentrations will vary according to the particular sugar used, for example, for monosaccharides the final concentration should be about 5.0% w/v, for disaccharides about 10.0% w/v. In addition, formulations may be made with sugar/salt combinations, such as 2.5% w/v glucose with 0.45% w/v NaCl, or 5.0% w/v sucrose with 0.45% w/v NaCl. The thus formulated IgG solution is filtered through 0.2-0.5 micron pads or cartridges, such as Cuno 60SP or Cuno IDEP, followed by filtration through a series of clarification and sterilization filters having a porosity of from 1.5 to 0.2 microns.

It is to be noted that the process of the present invention may be used to prepare a variety of hyperimmune globulin products containing hyperimmune globulin against one or more serotypes of *Pseudomonas aeruginosa*. In addition, the purfication process may also be used for obtaining highly purified hyperimmune gloublin that is effective against other pathogens. Still further, it is also contemplated that polyvalent immune globulin products for intravenous use having increased titers against at least two, but preferably against all sixteen, serotypes of *Pseudomonas aeruginosa* produced by the method of the present invention or by other appropriate art recognized methods are within the purvue of the present invention.

The following examples further illustrate the invention:

EXAMPLE 1

1 Kg Cohn Fraction II paste was suspended in 10 liters of cold purified water. The pH was adjusted to 7.5 and the suspension was allowed to stand for 4 hrs. at 2±1.0° C. The precipitate which contains aggregated IgG, IgM, PKa, plasminogen and other trace contaminants was removed by centrifugation at 3000×g for 20 min. or by filtration through a 0.2-0.5 micron filter pads such as Cuno 60 SP. The solution was adjusted to pH 6.8, stabilized by adding albumin at a ratio of 2 parts IgG to 1 part albumin, concentrated, diafiltered using 0.2% w/v NaCl and formulated by adding the desired sugar and/or salt. The solution was readjusted to pH 6.8 and diluted to a solution that had a final concentration of 5.0% w/v IgG with the desired concentration of salt and/or sugar.

EXAMPLE 2

1 Kg Cohn Fraction II was suspended in 15 liters of a cold purified water ethanol solution so that the final alcohol concentration was 4% w/v. The pH was adjusted to 7.6 and the suspension was allowed to stand for 2 hrs. at 2±1.0° C. The precipitate was removed, albumin was added at a ratio of 2 parts IgG to 1 part albumin, concentrated, diafiltered at constant volume using 0.2% w/v NaCl, and formulated by adding the desired sugar and/or salt. The pH was adjusted to 6.8 and the solution is diluted to a 5% w/v solution which contained the desired concentration of salt and/or sugar.

EXAMPLE 3

1 Kg Cohn Fraction II was suspended at 15 liters of cold water and alcohol was added to the suspension to obtain a final concentration of 4% w/v alcohol. The suspension was adjusted to pH 7.6 and allowed to stand for 2 hrs. at 2±1.0° C. The precipitate as removed and the filtrate was adjusted to pH 6.8. Albumin is added at a ratio of 1 to 2. The solution was concentrated, diafiltered at constant volume using cold Pyrogen Free water. The solution was diluted to a 5% w/v IgG solution which contained the desired concentration of salt and/or sugar. The pH of the solution was readjusted to pH 6.8, passed through clarification and sterilization filters, aseptically filled into sterile bottles, stoppered and sealed.

EXAMPLE 4

1 Kg Cohn Fraction II was suspended in 20 liters of a cold purified water-ethanol solution so that the final alcohol concentration was 4% w/v. The pH was adjusted to pH 7.4 and the suspension is allowed to stand 16 hrs. at 2±1.0° C. The precipitate was removed and the filtrate was adjusted to pH 6.8. Albumin was added at a ratio of 1—1 and the solution was concentrated and diafiltered at constant volume using 10 volumes of cold Pyrogen Free water at 2±1.0° C. The solution was then formulated by adding the desired sugar and/or salt. The pH was readjusted to 6.8 and the solution was diluted to contained a 5% w/v IgG solution that contains the desired concentration of salt and/or sugar.

EXAMPLE 5

Native IgG was isolated from a pool of plasma obtained from 15 non-immunized donors by Cohn fractionation and purification according to the process of the present invention. Antibody titers of the pooled plasma and the purified gamma globulin were measured. Side-by-side results of titers for plasma and IgG are shown for all 16 serotypes of *Ps. aeruginosa* in Table IV.

TABLE IV

| | Antibody Titers of Plasma and Pure IgG of Non-Immunized Donors | |
|---|---|---|
| Serotype | Plasma Pool Titer (approx. 1% IgG) | Titer/1% Purified IgG |
| 1 | 100 | 200 |
| 2 | 400 | 200 |
| 3 | 400 | 200 |
| 4 | 100 | 100 |
| 5 | 400 | 400 |
| 6 | 25 | 200 |
| 7 | 100 | 100 |
| 8 | 100 | 100 |
| 9 | 200 | 100 |
| 10 | 200 | 200 |
| 11 | 200 | 200 |
| 12 | 50 | 100 |
| 13 | 25 | 100 |
| 14 | 400 | 400 |
| 15 | 100 | 200 |
| 16 | 200 | 200 |

EXAMPLE 6

Native IgG was isolated from a large commercial pool (about 2,000 donors) of normal, non-immunized donors and processed as in Example 5. Antibody titers of the purified gamma globulin were measured. Results are shown for all 16 serotypes of *Ps. aeruginosa* Table V.

TABLE V

| Serotype | Titer/1% Purified IgG |
|---|---|
| 1 | 400 |
| 2 | 400 |
| 3 | 400 |
| 4 | 200 |
| 5 | 800 |
| 6 | 200 |
| 7 | 200 |
| 8 | 200 |
| 9 | 200 |
| 10 | 100 |
| 11 | 400 |
| 12 | 200 |
| 13 | 200 |
| 14 | 400 |
| 15 | 200 |
| 16 | 400 |

EXAMPLE 7

Thirteen low-response donors that were immunized with polyvalent pseudomonas vaccine were selected for plasmapheresis at three weeks post vaccination. Native IgG was isolated from the plasma pool obtained from these donors as in Example 5. Antibody titers of the pooled plasma and the purified gamma globulin were measured. Side-by-side results of titers for plasma and IgG are shown for all 16 serotypes in Table VI.

TABLE VI

| | Low-response Donors (3 weeks post-vaccination) | |
|---|---|---|
| Serotype | Plasma Pool Titer | Titer/1% Purified IgG |
| 1 | 800 | 400 |
| 2 | 800 | 800 |
| 3 | 400 | 800 |
| 4 | 400 | 400 |
| 5 | 800 | 400 |
| 6 | 200 | 400 |
| 7 | 400 | 400 |
| 8 | 400 | 400 |
| 9 | 400 | 400 |
| 10 | 400 | 400 |
| 11 | 800 | 800 |
| 12 | 400 | 800 |
| 13 | 400 | 200 |
| 14 | 400 | 800 |
| 15 | 400 | 400 |
| 16 | 400 | 800 |

EXAMPLE 8

Thirteen high-response donors that were immunized with polyvalent pseudomonas vaccine were selected for plasmapheresis at three weeks post-vaccination. Native IgG was isolated from the plasma pool obtained from the donors as described in Example 5. Antibody titers of the pooled plasma and the purified gamma globulin were measured. Side-by-side results of titers for plasma and IgG are shown for all 16 serotypes in Table VII.

TABLE VII

| | High-response Donors (3 weeks post-vaccination) | |
|---|---|---|
| Serotype | Plasma Pool Titer | Titer/1% Purified IgG |
| 1 | 800 | 800 |
| 2 | 800 | 1600 |
| 3 | 800 | 800 |
| 4 | 800 | 800 |
| 5 | 1600 | 1600 |
| 6 | 800 | 800 |
| 7 | 800 | 800 |
| 8 | 800 | 1600 |
| 9 | 800 | 800 |
| 10 | 1600 | 1600 |
| 11 | 800 | 1600 |
| 12 | 1600 | 3200 |
| 13 | 800 | 800 |
| 14 | 1600 | 3200 |
| 15 | 800 | 1600 |
| 16 | 1600 | 1600 |

EXAMPLE 9

Fifteen high-response donors that were immunized with polyvalent pseudomonas vaccine were selected for plasmapheresis at three weeks post-vaccination. Native IgG was isolated from the plasma pool obtained from the donors as described in Example 5. Antibody titers of the pooled plasma and the purified gamma globulin were measured. Side-by-side results of titers for plasma and IgG are shown for all 16 serotypes in Table VIII.

TABLE VIII

| | High-response Donors (3 weeks post-vaccination) | |
|---|---|---|
| Serotype | Plasma Pool Titer | Titer/1% Purified IgG |
| 1 | 800 | 800 |
| 2 | 800 | 800 |
| 3 | 800 | 800 |
| 4 | 800 | 800 |
| 5 | 800 | 800 |
| 6 | 400 | 800 |
| 7 | 400 | 800 |
| 8 | 800 | 800 |
| 9 | 800 | 800 |
| 10 | 800 | 1600 |
| 11 | 800 | 800 |
| 12 | 800 | 1600 |
| 13 | 800 | 800 |
| 14 | 1600 | 1600 |
| 15 | 800 | 1600 |
| 16 | 800 | 1600 |

EXAMPLE 10

Fifteen high-response donors that were immunized with polyvalent pseudomonas vaccine were selected for plasmapheresis at eighteen weeks post-vaccination. Native IgG was isolated from the plasma pool obtained from these donors as described in Example 5. Antibody titers of the pooled plasma and the purified gamma globulin were measured. Side-by-side results of titers for plasma and IgG are shown for all 16 serotypes in Table IX.

TABLE IX

| | High-response Donors (18 weeks post-vaccination) | |
|---|---|---|
| Serotype | Plasma Pool Titer | Titer/1% Purified IgG |
| 1 | 400 | 400 |
| 2 | 800 | 400 |
| 3 | 800 | 400 |
| 4 | 400 | 400 |
| 5 | 400 | 800 |
| 6 | 200 | 200 |
| 7 | 400 | 400 |
| 8 | 400 | 400 |
| 9 | 400 | 400 |
| 10 | 400 | 400 |
| 11 | 400 | 400 |
| 12 | 400 | 800 |
| 13 | 400 | 200 |
| 14 | 400 | 800 |
| 15 | 400 | 400 |
| 16 | 400 | 800 |

EXAMPLE 11

IgG obtained in Examples 5, 6, 7, 9 and 10 were studied to determine their efficacy in the burned mouse model based on Stieritz & Holder (J. Infect. Dis. 131: 688-691, 1975). As apparent from Tables X and XI, antibody titers tend to correlate with survival of the mice infected with $10^6$ Ps. aeruginosa.

TABLE X

Survival of Burned, Infected Mice Treated With Various Intravenous IgG Preparations (5 mg)

| Treatment | Examples | Infective Dose | % Survival 5 Days | Serotype 2/5 Titer |
|---|---|---|---|---|
| None | | $10^6$ Ps. aeruginosa Serotype 2/5 | 0 | 50 |
| Albumin | | $10^6$ Ps. aeruginosa Serotype 2/5 | 0 | 50 |
| Normal Gamma Globulin 15 Donors | 5 | $10^6$ Ps. aeruginosa Serotype 2/5 | 20 | 1350 |
| Normal I.V. Gamma Globulin | 6 | $10^6$ Ps. aeruginosa Serotype 2/5 | 60 | 2300 |
| 3 Weeks Post Vaccination 13 Refractory Donors | 7 | $10^6$ Ps. aeruginosa Serotype 2/5 | 60 | 2300 |
| 3 Weeks Post Vaccination 15 Responsive Donors | 9 | $10^6$ Ps. aeruginosa Serotype 2/5 | 80 | 5600 |
| 18 Weeks Post Vaccination 15 Responsive Donors | 10 | $10^6$ Ps. aeruginosa Serotype 2/5 | 60 | 2300 |

TABLE XI

Survival of Burned, Infected Mice Treated With Various Intravenous IgG Preparations (5 mg)

| Treatment | Examples | Infective Dose | % Survival 5 Days | Serotype 6 Titer |
|---|---|---|---|---|
| None | | $10^6$ Ps. aeruginosa Serotype 6 | 0 | 50 |
| Albumin | | $10^6$ Ps. aeruginosa Serotype 6 | 0 | 50 |
| Normal Gamma Globulin 15 Donors | 5 | $10^6$ Ps. aeruginosa Serotype 6 | 0 | 700 |
| Normal I.V. Gamma Globulin | 6 | $10^6$ Ps. aeruginosa Serotype 6 | 0 | 700 |
| 3 Weeks Post Vaccination 13 Refractory Donors | 7 | $10^6$ Ps. aeruginosa Serotype 6 | 40 | 900 |
| 3 Weeks Post Vaccination 15 RESPONSIVE DONORS | 9 | $10^6$ Ps. aeruginosa Serotype 6 | 40 | 1800 |
| 18 Weeks Post Vaccination 15 Responsive Donors | 10 | $10^6$ Ps. aeruginosa Serotype 6 | 60 | 3600 |

The products obtained by the foregoing examples, and products made according to the teaching of the specification, in addition to having been tested for antibody titers and efficacy as previously described, were tested by using appropriate procedures for verifying and defining other characteristics of IgG products. In general, the following qualities characterized the products of the present invention when analyzed according to the methods identified below.

A product of the present invention is at least 99% pure immune gamma globulin; it is essentially free of IgA and IgM as measured by Radial Immune Diffusion (RID) according to Mancini, G., Caronara, A. D., Hermans Immuno-chemistry 2 235 (1975) and by the laser nephelometry method based on antibody-antigen complex measurements as described by Schultz et al., J. Immunological Methods 31 31–40 (1979). No plasmin or plasminogen were detected by the use of streptokinase and CBZ-lyz-P-nitrophenol, as described by the method by Silverstein, R. M. Analytical Biochemistry 65 500–506 (1975).

Anticomplement activity (ACA) is less than 0.10 C'50 units mg IgG as measured by a modified method of Kabet, E. A. and Mayer, M. Experimental Immunochemistry, Second Edition, Thomas Springfield (1961). Aggregated IgG was not detected when the product was assayed either by high performance liquid chromatograph (HPLC) using a TSK 3000 SW column or by gel permeation chromatograph using a 90 cm. column packed with LKB ultragel AcA 34. The product does not contain detectable hepatitis surface antigen B when measured by the radioimmune assay using RIASURE II test kit obtained from Electro-Nucleonics Laboratories, Inc. The product contains all the subtypes of IgG, namely $IgG_1$, $IgG_2$, $IgG_3$, and $IgG_4$, and the percentage for each of these subtypes is about 64%, 29%, 6%, and 1% respectively, which is essentially identical to the percent distribution found in the Cohn Fraction II paste as measured by Radial Immune Diffusion (RID) method referred to above. The antibody titers for measles, polio, diphtheria and hepatitis were equivalent to the titers found in the commercial intramuscular immune serum globulin products.

As earlier indicated, the pure IgG molecule obtained according to the method of the present invention is formulated into pharmaceutical dosage forms suitable for intravenous administration. Such dosage forms include the lyophilized form and the liquid dosage form of IgG.

In the lyophilized dosage form a pharmaceutically acceptable sugar such as maltose, sucrose or glucose is added to the pure product to protect the IgG and to provide bulk during freezing and lyophilization. An example for such lyophilized composition is given in Example 12, which was found to be stable for at least one year at both refrigeration and room temperatures with no change in anticomplement activity which averaged between 0.03 to 0.04 C'50 units/mg. No aggregates or fragments were detected.

EXAMPLE 12

| Ingredients | gms/50 ml |
|---|---|
| Immune Globulin | 2.5 |
| Normal Serum Albumin | 1.25 |
| Sodium Chloride | 0.1 |
| Maltose | 5.0 |
| Water for Injection* | q.s. to 50 ml |

(*water is removed by freeze-drying)

Examples 13, 14 and 15 show liquid dosage formulations containing 5% w/v IgG and 2.5% w/v Normal Serum Albumin with either 10% maltose, 5% sucrose, or no carbohydrate. Appropriate amounts of sodium chloride was added in each case to make the preparations iso-osmotic.

Upon testing the maltose-containing IgG was found to be stable at room temperature for 6 months and at refrigeration temperatures for at least a year. The anticomplement activity did not change significantly from the initial levels and averaged between 0.025 and 0.045 C'50 units/mg. In addition, no aggregates or fragments were detected. The liquid formulations of IgG containing sucrose or no carbohydrates were found to be stable for at least 6 months at both refrigeration and room temperatures. The anticomplement activity did not change significantly from the initial levels, and averaged between 0.07 and 0.1 C'50 units/mg. As with the previous fromulation, no aggregate or fragments were detected.

EXAMPLE 13

| Ingredients | gms/50 ml |
|---|---|
| Immune Globulin | 2.5 |
| Normal Serum Albumin | 1.25 |
| Sodium Chloride | 0.1 |
| Maltose | 5.0 |

-continued

| Ingredients | gms/50 ml |
|---|---|
| Water for Injection | q.s. to 50 ml |

EXAMPLE 14

| Ingredients | gms/50 ml |
|---|---|
| Immune Globulin | 2.5 |
| Normal Serum Albumin | 1.25 |
| Sodium Chloride | 0.25 |
| Sucrose | 2.5 |
| Water for Injection | q.s. to 50 ml |

EXAMPLE 15

| Ingredients | gms/50 ml |
|---|---|
| Immune Globulin | 2.5 |
| Normal Serum Albumin | 1.25 |
| Sodium Chloride | 0.45 |
| Water for Injection | q.s. to 50 ml |

Specific results on formulations prepared according to the present invention are shown in Table XII.

TABLE XII
Analysis of IV-IGG Lots Immuneglobulin Composition

| Lot No. | Description | % IgG | % IgA | % IgM | ACA C'50 U/mg | Mol. Size % Aggregate |
|---|---|---|---|---|---|---|
| 1 | Lyophylized 10% Maltose | 100 | 0 | 0 | 0.040 | 0 |
| 2 | 10% Maltose | 99.87 | 0.03 | 0 | 0.049 | 0 |
| 3 | 5% Glucose | 99.97 | 0.03 | 0 | 0.053 | 0 |
| 4 | 10% Maltose | 100 | 0 | 0 | 0.045 | 0 |
| 5 | 10% Maltose | 99.97 | 0.03 | 0 | 0.030 | 0 |
| 6 | Saline | 99.97 | 0.03 | 0 | 0.082 | 0 |
| 7 | 5% Sucrose | 99.96 | 0.04 | 0 | 0.077 | 0 |
| 8 | Saline | 100 | 0 | 0 | 0.088 | 0 |
| 9 | 10% Maltose | 99.95 | 0 | 0 | 0.033 | 0 |
| 10 | 10% Maltose | 99.91 | 0.09 | 0 | 0.041 | 0 |
| 11 | 5% Maltose | 99.96 | 0.04 | 0 | 0.087 | 0 |

Table XIII shows an analysis of IgG of the present invention versus that of commercial products.

TABLE XIII
ANALYSIS OF IgG of the PRESENT INVENTION VS COMMERCIAL IgG PRODUCTS

| Manufacturer | IgG Mg/dl | IgA mg/dl | IgM mg/dl | IgG$_1$ | IgG$_2$ % | IgG$_3$ % | IgG$_4$ % | ACA C'50/mg | Pka % of BOB Ref. 2* |
|---|---|---|---|---|---|---|---|---|---|
| Commercial Product 1 | 4660 | 5.7 | 0 | 52.9 | 41.9 | 4.01 | 1.18 | 0.046 | 4.8 |
| Commercial Product 2 | 2520 | 35.3 | 9.3 | 78.5 | 11.1 | 6.98 | 3.36 | 0.062 | 6.5 |
| Commercial Product 3 | 4687 | 0 | 5.5 | 55.6 | 38.0 | 1.5 | 4.71 | 0.087 | 58.4 |
| Commercial Product 4 | 5070 | 28.4 | 36 | 72.86 | 25.76 | 0 | 1.38 | 0.015 | 31.0 |
| Present Invention | 5520 | 0 | 0 | 63.6 | 28.6 | 6.3 | 1.5 | 0.045 | 0.26 |

*% of Pka (Pre-Kallicrein Activator) obtained from the FDA office of Biologics.

The formulations of the present invention are administered intravenously. Generally, an amount of 1 to 10 gm of gamma globulin may be used at a time. However, the dose of gamma-globulin for use in intravenous administration depends on the age, physical condition, antibody titer of the particular formulation, etc. and as such the physician will determine the particular dose suitable for effecting treatment based on his considering the various factors and circumstances.

It is apparent that numerous modifications and variations of the invention may be made without departing from the spirit and scope thereof. The specific embodiments described are given by way of example only and the invention is limited only by the scope of the appended claims.

What is claimed is:

1. A process for the preparation of an unmodified, native gamma immune globulin for intravenous administration comprising the steps of:
   a., suspending of IgG Cohn Fraction II in an aqueous solution of about 2 to 10% w/v ethanol at a protein concentration of about 1 to 4% w/v at a temperature of 2°–5° C.;
   b., adjusting the pH of the suspension to about 7.6±0.2;
   c., adding NaCl to the suspension to obtain salt concentration of 0 to 2 mM NaCl;
   d., allowing the suspension to stand for 6 to 18 hrs. to precipitate IgM, IgA, enzymes, polymeric forms of IgG impurities and to obtain equilibrium between precipitated impurities and dissolved IgG;
   e., removing the precipitated impurites to obtain a dilute IgG solution;
   f., stabilizing the dilute IgG solution by adding Human Serum Albumin to obtain an IgG/albumin ratio of 1/1 to 2/1;
   g., adjusting NaCl concentration of the solution to 0 to 0.9% w/v NaCl;
   h., adjusting the pH of the solution to about 6.9±0.4;
   i., concentrating the solution by ultrafiltration to obtain a concentration of about 4% w/v IgG;
   j., removing the ethanol and concentrating the solution to about 4 to 6% w/v IgG by diafiltration; and
   k., formulating the solution with the addition of sodium chloride, carbohydrates or combinations thereof.

2. The process of claim 1 wherein said Cohn Fraction II is obtained from pooled plasma of *Pseudomonas aeruginosa* immunized donors.

3. The process of claim 1 wherein said Cohn Fraction II is about 95% pure, native gamma globulin.

4. The process of claim 1 wherein said Cohn Fraction II is about 95% pure, native hyperimmune globulin.

5. The process of claim 3 wherein said 95% pure native gamma globulin comprises $IgG_1$, $IgG_2$, $IgG_3$ and $IgG_4$.

6. The process of claim 1 wherein the precipitated impurities are removed by filtration.

7. The process of claim 1 wherein the precipitated impurities are removed by centrifugation.

8. The process of claim 1 wherein the IgG solution is formulated with NaCl to obtain a final concentration of about 0–0.9% w/v NaCl.

9. The process of claim 1 wherein the IgG solution has a carbohydrate concentration of about 2.5 to 10% w/v.

10. The process of claim 9 wherein said carbohydrate is glucose.

11. The process of claim 9 wherein said carbohydrate is sucrose.

12. The process of claim 1 wherein said unmodified, native, immune globulin is hyperimmune globulin.

* * * * *